US009603969B2

(12) United States Patent
Nakada et al.

(10) Patent No.: US 9,603,969 B2
(45) Date of Patent: Mar. 28, 2017

(54) POROUS SCAFFOLD MATERIAL, AND METHOD FOR PRODUCING SAME (75) Inventors: Akira Nakada, Kyoto (JP); Keiji Shigeno, Kyoto (JP); Tatsuo Nakamura, Kyoto (JP)

(73) Assignee: Kyoto University, Kyoto (JP)

( * ) Notice: Subject to any disclaimer, the term of this patent is extended or adjusted under 35 U.S.C. 154(b) by 89 days.

(21) Appl. No.: 14/241,866

(22) PCT Filed: Aug. 29, 2012

(86) PCT No.: PCT/JP2012/071902
§ 371 (c)(1),
(2), (4) Date: Feb. 27, 2014

(87) PCT Pub. No.: WO2013/031861
PCT Pub. Date: Mar. 7, 2013

(65) Prior Publication Data
US 2014/0221615 A1  Aug. 7, 2014

(30) Foreign Application Priority Data
Aug. 30, 2011  (JP) .................................. 2011-187228

(51) Int. Cl.
| *A61K 38/39* | (2006.01) |
| *A61L 27/56* | (2006.01) |
| *A61L 15/32* | (2006.01) |
| *A61L 27/24* | (2006.01) |
| *A61L 27/50* | (2006.01) |
| *A61K 38/00* | (2006.01) |

(52) U.S. Cl.
CPC .............. *A61L 27/24* (2013.01); *A61L 27/50* (2013.01); *A61L 27/56* (2013.01); *A61L 2400/00* (2013.01)

(58) Field of Classification Search
CPC .......... A61L 27/56; A61F 2310/00371; A61F 2002/30766
See application file for complete search history.

(56) References Cited

U.S. PATENT DOCUMENTS

| 5,681,353 A | 10/1997 | Li et al. | |
|---|---|---|---|
| 5,735,903 A | 4/1998 | Li et al. | |
| 6,042,610 A | 3/2000 | Li et al. | |
| 6,964,685 B2* | 11/2005 | Murray | A61L 24/043 623/13.17 |
| 8,128,984 B2* | 3/2012 | Knight | A61L 27/3604 427/2.26 |
| 2003/0015825 A1 | 1/2003 | Sugie et al. | |
| 2004/0054410 A1 | 3/2004 | Barrows | |
| 2006/0276900 A1* | 12/2006 | Carpenter | A61F 2/442 623/17.15 |
| 2007/0009585 A1 | 1/2007 | Morinaga et al. | |
| 2008/0020049 A1* | 1/2008 | Darling | A61L 27/38 424/489 |
| 2008/0206297 A1* | 8/2008 | Roeder | A61F 2/28 424/422 |
| 2009/0012627 A1* | 1/2009 | Claesson | A61L 27/48 623/23.72 |
| 2009/0149634 A1 | 6/2009 | Shoji et al. | |
| 2009/0275129 A1* | 11/2009 | Cooper | A61L 27/18 435/366 |
| 2009/0280161 A1 | 11/2009 | Nakamura et al. | |
| 2010/0324658 A1* | 12/2010 | Bogert | A61F 2/91 623/1.16 |
| 2011/0177151 A1* | 7/2011 | Knight | A61L 27/3604 424/423 |
| 2012/0245540 A1* | 9/2012 | Zimnitsky | A61K 31/385 604/319 |

FOREIGN PATENT DOCUMENTS

| EP | 1273615 A1 | 1/2003 | |
|---|---|---|---|
| JP | 2007-037965 A | 2/2007 | |
| JP | 2009-132601 A | 6/2009 | |
| WO | WO 95/32623 A1 | 12/1995 | |
| WO | WO 00/61045 A1 | 10/2000 | |
| WO | WO 02/09790 A1 | 2/2002 | |
| WO | WO 02/15952 A1 | 2/2002 | |
| WO | WO 2007035778 A2 * | 3/2007 | ............. A61L 27/24 |
| WO | WO 2008/001952 A1 | 1/2008 | |

OTHER PUBLICATIONS

Saglam A (2010) "Scaffolds with Oriented Microchannels for Angioneural Regenerative Engineering", A Thesis, Drexel University, pp. 1-71.*
Akita et al., *Stem Cells International*, 2010, Article ID 532704, pp. 1-8 (2010).
Bushnell et al., *Journal of Hand Surgery*, 33(7): 1081-1087 (2008).
Chen et al., *Biomechanics at Micro and Nanoscale Levels*, 3: 118-129 (2007).
Kato et al., *European Journal of Cardio-thoracic Surgery*, 35(1): 37-42 (2009).
Nakamura et al., *Surgery Today*, 40(8): 734-737 (2010).
Ueda et al., *Journal of Thoracic Cardiovascular Surgery*, 139(3): 600-605 (2010).
Japanese Patent Office, International Search Report in International Patent Application No. PCT/JP2012/071902 (Nov. 13, 2012).
European Patent Office, Extended European Search Report in European Patent Application No. 12827464.4 (Jun. 26, 2015).
Dagalakis et al., *Journal of Biomedical Materials Research*, 14: 511-528 (1980).
Yannas et al., *Journal of Biomedical Materials Research*, 14: 107-131 (1980).

(Continued)

*Primary Examiner* — Anand Desai
*Assistant Examiner* — Samuel Liu
(74) *Attorney, Agent, or Firm* — Leydig, Voit & Mayer, Ltd.

(57) ABSTRACT

Provided are a scaffold material that functions as a scaffold material for two weeks or more in vivo and causes substantially no foreign-body reaction, and a method for producing the scaffold material. Specifically, a porous scaffold material comprising collagen fibers is provided.

6 Claims, 8 Drawing Sheets

(56) References Cited

OTHER PUBLICATIONS

Yannas et al., *Trans. Soc. Biomaterials* (*The 11$^{th}$ Annual Meeting of the Society for Biomaterials on Apr. 25-28, 1985*), 8: 146 (1985).

\* cited by examiner

POROUS SCAFFOLD MATERIAL, AND METHOD FOR PRODUCING SAME

CROSS-REFERENCE TO RELATED APPLICATIONS

This patent application is the U.S. national phase of International Patent Application No. PCT/JP2012/071902, filed Aug. 29, 2012, which claims the benefit of Japanese Patent Application No. 2011-187228, filed on Aug. 30, 2011, which are incorporated by reference in their entireties herein.

TECHNICAL FIELD

The present invention relates to a porous scaffold material comprising collagen fibers, and to a method for producing the same.

BACKGROUND ART

Various materials have been developed as "scaffolds" to be used for regenerative medicine. Typical examples of the materials may include synthetic polymers such as poly-glycolic acid (PGA), poly-L-lactic acid (PLLA), and poly-lactic-co-glycolic acid (PLGA) as a complex thereof; and natural polymers such as collagen and gelatin. These materials have already been used in clinical practice and have yielded definite results (Non-patent Literature 1 to 4). However, for example, use of the poly-glycolic acid in vivo may induce an inflammatory reaction due to a local reduction in pH, resulting in needless adhesion (Non-patent Literature 5). In addition, collagen has tissue compatibility but may cause a problem of insufficient durability for some organs or sites to be regenerated (Non-patent Literature 6).

CITATION LIST

Non-Patent Literature

NPL 1: Kato, Y., et al., A novel technique to prevent intra-operative pneumothorax in awake coronary artery bypass grafting: biomaterial neo-pleura. European Journal of Cardio-Thoracic Surgery: official journal of the European Association for Cardio-thoracic Surgery, 2009. 35(1): pp. 37-41.

NPL 2: Ueda, K., et al., Sutureless pneumostasis using bioabsorbable mesh and glue during major lung resection for cancer: who are the best candidates? The Journal of Thoracic and Cardiovascular Surgery, 2010. 139(3): pp. 600-5.

NPL 3: Akita, S., et al., Noncultured autologous adipose-derived stem cells therapy for chronic radiation injury. Stem Cells International, 2010. 2010: p. 532704.

NPL 4: Bushnell, B. D., et al., Early clinical experience with collagen nerve tubes in digital nerve repair. The Journal of Hand Surgery, 2008. 33(7): pp. 1081-7.

NPL 5: T. Nakamura, et al., An evaluation of the surgical morbidity of polyglycolic acid felt in pulmonary resections. Surgery Today, 2010. 40(8): pp. 734-737.

NPL 6: G. Chen, et al., Scaffolding technology for cartilage and osteochondral tissue engineering. Biomechanics at Micro- and Nanoscale Levels 3, 2007: pp. 118-129.

SUMMARY OF INVENTION

Technical Problem

An object of the present invention is to provide a scaffold material that functions as a scaffold material for two weeks or more in vivo and causes substantially no foreign-body reaction, and to provide a method for producing the scaffold material.

Solution to Problem

The present invention provides the following scaffold materials and methods for producing the same.

Item 1. A porous scaffold material comprising collagen fibers orientated in one direction, pores being formed along the orientation direction of the collagen fibers, the porous scaffold material causing substantially no foreign-body reaction for at least two weeks when embedded into a living body, the porous scaffold material functioning as a scaffold material for at least two weeks in vivo.

Item 2. The porous scaffold material according to Item 1, wherein the porous scaffold material has a compression modulus of elasticity of from 0.05 to 1.0 MPa.

Item 3. The porous scaffold material according to Item 2, wherein the porous scaffold material has a compression modulus of elasticity of from 0.17 to 0.6 MPa.

Item 4. The porous scaffold material according to any one of Items 1 to 3, wherein the porous scaffold material has a pore diameter of from 50 to 500 μm.

Item 5. The porous scaffold material according to any one of Items 1 to 4, wherein the collagen fibers include atelocollagen fibers.

Item 6. The porous scaffold material according to any one of Items 1 to 5, wherein the porous scaffold material contains almost no foreign-body giant cells or no foreign-body giant cells.

Item 7. The porous scaffold material according to any one of Items 1 to 6, wherein the porous scaffold material is produced by placing a collagen fiber suspension in a container; and cooling the collagen fiber suspension only from the bottom surface, followed by freeze drying and thermal denaturation.

Item 8. A method for producing a porous scaffold material of any one of Items 1 to 7 comprising: placing a collagen fiber suspension in a neutral region in a container; and cooling the collagen fiber suspension only from the bottom surface, followed by freeze drying and thermal denaturation.

Item 9. The method according to Item 8, wherein the thermal denaturation is carried out at a temperature of from 120° C. to 150° C.

Item 10. The method according to Item 8 or 9, wherein a freezing temperature of the collagen fiber suspension is from −5° C. to −80° C.

Advantageous Effects of Invention

The scaffold material of the present invention remains and functions as a scaffold material for two weeks or more in vivo while containing substantially no foreign-body giant cells and causing no foreign-body reaction.

The scaffold material of the present invention can have increased strength without causing any foreign-body reaction. Thus, scaffold materials having various strengths can be produced depending on sites into which the materials are embedded.

The infiltration property of cells into the scaffold material is enhanced and the tissue compatibility of the scaffold material is improved by providing orientation to the collagen fibers in the scaffold material. The scaffold material of the present invention is useful as a scaffold for the regeneration of all tissues.

The scaffold material of the present invention is infiltrated with a large number of cells, blood vessels, and the like from its surroundings so as to integrate with the surrounding tissue. Thus, the scaffold material of the invention is very effective for tissue repair and the like.

BRIEF DESCRIPTION OF DRAWINGS

FIG. 1 illustrates the properties of collagen at different temperatures and pH values. When heat is applied to collagen derived from a homeothermal animal on land in an aqueous solution state, a phenomenon in which three polypeptide chains are disentangled, called "denaturation", starts to occur gradually from the point at which the temperature exceeds 30° C., and half of the polypeptide chains are disentangled at around 40° C. in a neutral region. Then, when heated at higher temperature, the collagen molecules are thermally denatured to form gelatin. Once formed, it is difficult to return the gelatin to the collagen molecules.
a. An assembly of collagen microfibrils (bundles of five collagen molecules). The collagen fibrils further assemble to form collagen fibers.
b. By heating at higher temperature, a helical structure is completely broken to form gelatin (sol state). When the gelatin is cooled, the neighboring polypeptide chains partially form a helical structure to solidify as a gel. However, it is difficult to completely return the gelatin to the original collagen molecules.

FIG. 3 shows a container for providing collagen fibers with orientation.
a: (i) an outer frame made of styrene foam, (ii) an aluminum plate, (iii) a lid made of styrene foam, (iv) a Parafilm, and (v) an inner frame made from a paper measuring cup.
b: An aluminum plate is attached to the bottom of the outer frame with a vinyl tape, and the inner frame is further installed.
c: The resultant is covered with the Parafilm. A collagen fiber suspension undergoes volume expansion at the time of freezing and may touch the lid made of styrene foam. In that case, there is possibility that collagen will be contaminated with fine fibers in the styrene foam, and the covering of Parafilm is carried out to prevent this.
d: The resultant is covered with the lid made of styrene foam and fixed with vinyl tape. Cooling is applied only from the lower surface of the container, thereby providing orientation to the collagen fiber scaffold material.

FIG. 6 show a collagen fiber scaffold material subjected to thermal denaturation processing (two weeks after the embedding under the skin).
a. 140° C. for six hours: Almost no foreign-body giant cells were identified. Thus, a compatibility score of 3 was given.
b. 140° C. for nine hours: Foreign body giant cells were identified here and there. Thus, a compatibility score of 2 was given. (The foreign-body giant cells are present in the part circled.)

DESCRIPTION OF EMBODIMENTS

Herein, any collagen such as type I, type II, type III, or type IV collagen may be used as collagen. These collagens may be used alone or as a mixture of two or more kinds. The collagen is preferably type I collagen. In a preferred embodiment of the present invention, the collagen may be type I collagen alone, or may be a collagen mixture of type I collagen with at least one kind of type II, type III, and type IV collagens. Atelocollagen may be preferably used as the collagen.

In the present invention, collagen fibers are used. The collagen fibers may be suspended in water having a pH in a neutral region. The pH in a neutral region is not particularly limited as long as the collagen fibers are present in a suspension state, but is, for example, about 6 to 8, preferably about 6.5 to 7.5, particularly preferably about 7 to 7.4. A collagen fiber suspension may be obtained by suspending collagen fibers in water or a buffer in a neutral region, or may be obtained by crushing a collagen mass constructed of collagen fibers, fiberizing the collagen mass with a mixer or the like, and then further processing the fibers to be disentangled with a homogenizer or the like. If the collagen mass is used, pores at the portion become small when a collagen fiber aggregate remains in the scaffold material. When the collagen fiber aggregate clogs the pores, cell infiltration stops there. Thus, it is recommended to disentangle the collagen fibers with a device such as a mixer or a homogenizer so as to prevent the generation of the collagen fiber aggregate as much as possible.

The pore diameter of the scaffold material of the present invention is 50 μm or more, preferably 70 μm or more, particularly preferably 100 μm or more. The upper limit of the pore diameter is not particularly limited but is, for example, about 500 μm, about 400 μm, about 300 μm, or about 200 μm. The pore diameter of the porous scaffold material is particularly preferably about 100 to 300 μm. With such pore diameter, the surrounding cells, blood vessels, and the like can sufficiently infiltrate the scaffold material to perform tissue regeneration. The pore diameter of the scaffold material may be confirmed with an electron micrograph such as a scanning electron microscope (SEM).

In the porous scaffold material of the present invention, the collagen fibers are preferably oriented. The orientation of the collagen fibers enhances the strength of the scaffold material and keeps the collagen fibers constituting pore walls from extending into the pores to promote the infiltration of cells and blood vessels into the scaffold material. The orientation of the collagen fibers may be confirmed with an electron micrograph such as an SEM. In conventional scaffold material including collagen as a constituent component, collagen molecules or collagen fibers were present at random. Thus, the speed at which cells, blood vessels, and the like infiltrate the scaffold material was low, and tissue regeneration proceeded only gradually. The scaffold material of the present invention remedied such drawbacks by using collagen fiber orientation. The scaffold material of the present invention preferably has the orientation structure shown in FIG. 13. The scaffold material of the present invention preferably includes collagen fibers orientated in one direction, and pores are formed along the orientation direction of the collagen fibers. When bundles of the collagen fibers are arranged at random, the bundles themselves serve as a barrier, which deteriorates the infiltration property of cells into the scaffold material. This is probably based on a mechanism different from a reduction in the infiltration property of the cells into the scaffold material accompanied by a foreign-body reaction, that is, physical inhibition. When the bundles of the collagen fibers are oriented, the physical inhibition of cell infiltration is eliminated, which makes it easier for the surrounding cells to infiltrate the scaffold material. Thus, tissue regeneration and reconstruction can be easily performed.

The scaffold material of the present invention has a compression modulus of elasticity of about 0.05 to 1.0 MPa, preferably about 0.1 to 0.8 MPa, more preferably about 0.17 to 0.6 MPa, still more preferably about 0.23 to 0.5 MPa, particularly preferably about 0.29 to 0.42 MPa. The compression modulus of elasticity may be calculated as a ratio between a stress and a strain in a straight line at a portion corresponding to a strain of 0.5 or near 0.5 in an elastic region on a stress-strain curve, which is obtained by carrying out compression at a speed of 1 mm/min with a compression tester until the load reaches 19 N.

The scaffold material of the present invention maintains its shape and functions as a scaffold material during the acute phase of two weeks after the embedding into a living body. When a scaffold material is embedded into a site requiring tissue regeneration, such as a tissue defect site, if the scaffold material can maintain its shape during the acute phase of about two weeks, tissue regeneration proceeds smoothly even when the scaffold material is absorbed and later disappears. Further, the scaffold material of the present invention causes almost no foreign-body reaction or no foreign-body reaction. This may be confirmed by the fact that the scaffold material contains almost no foreign-body giant cells or no foreign-body giant cells during the period of the acute phase of two weeks after the embedding into a living body. In order to enhance the strength of a scaffold material, previously, there a method has been employed involving subjecting a freeze-dried porous scaffold material to thermal processing or processing with a cross-linking agent to form cross-links between collagen fibers. However, the cross-links inevitably reduce the tissue compatibility of the scaffold material including collagen fibers to cause a foreign-body reaction. This is why it has not been possible to sufficiently perform tissue regeneration with the collagen scaffold material of the related art.

Even when a collagen scaffold material has pores sufficient for cell infiltration, cells do not infiltrate the pores if the tissue compatibility of the scaffold material is reduced by the cross-links. According to a preferred embodiment of the present invention, the scaffold material has improved strength by virtue of collagen fiber orientation and can be subjected to cross-linking processing required for shape maintenance under mild conditions during the period of the acute phase of two weeks after the embedding. With this, a foreign-body reaction can be reduced to a problem-free level, and tissue regeneration can be performed through the rapid infiltration of cells, blood vessels, and the like.

A method for producing the porous scaffold material of the present invention is described below.

Figure 1:
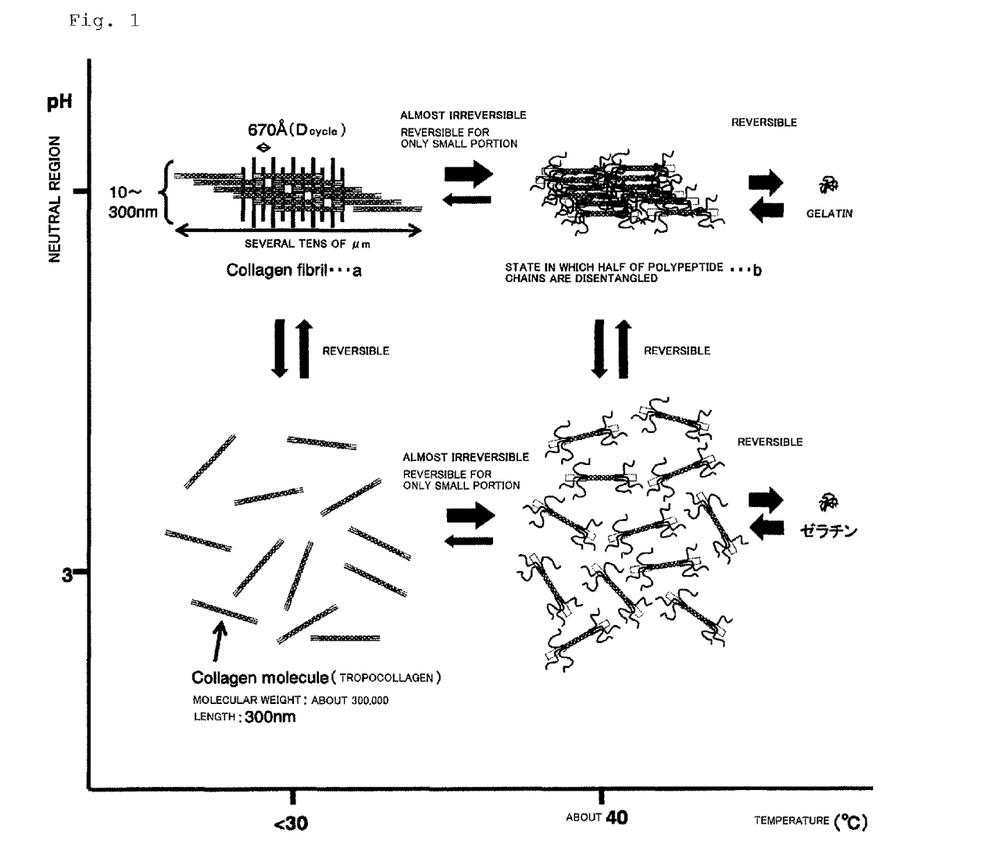
Figure 2:
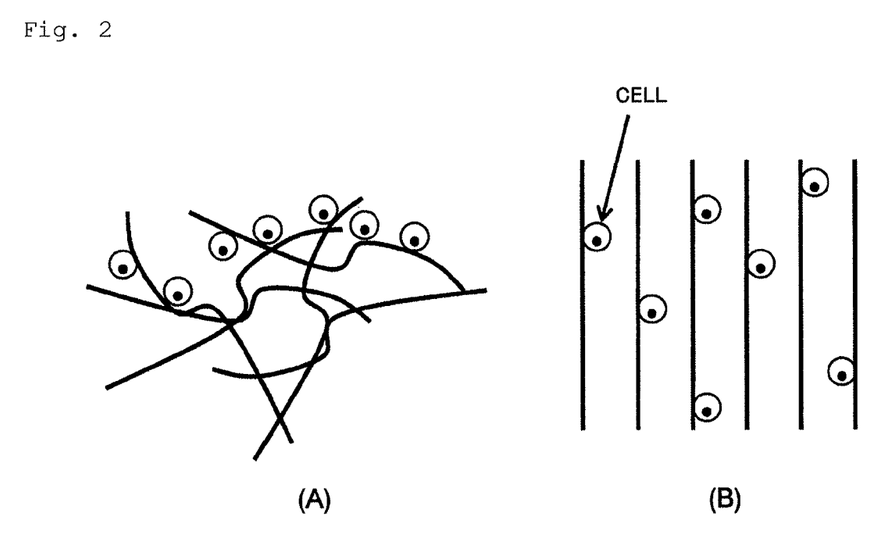
FIG. 2 illustrates a difference between a scaffold material with collagen fiber orientation and a scaffold material without collagen fiber orientation. In the case of no collagen fiber orientation, the infiltration of cells into the scaffold material occurs after the phagocytosis of collagen fibers. In the case of weakly denatured collagen fibers that have weak antigenicity and thus do not cause any foreign-body reaction at a problematic level, the fibers are excellent in durability. Thus, when the fibers are not subjected to any processing, it takes much time for cell infiltration. The scaffold material of the present invention has collagen fiber orientation and thus facilitates cell infiltration into the scaffold material (in both the cases of A and B, cells infiltrate the scaffold material along collagen fibers).

First, a collagen fiber suspension is prepared. Collagen exhibits a molecular structure in an acidic region and exhibits a fibrous structure in a neutral region, and the structures shift reversibly depending on the pH. Further, the collagen has a feature of being denatured to form gelatin through the disentanglement of polypeptide chains by heat. (FIG. 1; Peltonen, L., et al., Thermal stability of type I and type III procollagens from normal human fibroblasts and from a patient with osteogenesis imperfecta. Proceedings of the National Academy of Sciences of the United States of America, 1980. 77(1): pp. 162-6.) 40° C. in FIG. 1 refers to the "denaturation temperature" at which just half of the collagen molecules lose their structures in an aqueous solution or a suspension. The present invention provides a porous scaffold material including collagen fibers freeze-dried and then denatured by the application of heat at 40° C. or more. The thermal processing after the freeze drying forms cross-links. Accordingly, the scaffold material has increased strength and is excellent in durability in situ. On the other hand, a foreign-body reaction accompanying the cross-linking is at substantially non-problematic level. This may be confirmed by the fact that the scaffold material embedded into a living body contains almost no foreign-body giant cells.

Vertebrates such as cattle, swine, and chickens are examples of the source of the collagen. Collagen of any such source may be used. Two or more kinds of collagen may be used in combination.

The collagen fiber suspension is preferably prepared at a temperature such that denaturation does not occur (e.g., 37° C. or less). If commercially available collagen fibers are used, a collagen dispersion may be prepared by suspending the collagen fibers in water in a neutral region and uniformly dispersing the collagen fibers with a mixer, a homogenizer, or the like as required. When an aggregate or mass or the like of collagen fibers is used as a raw material, it is preferred to split the material to disentangle collagen fibers with water as a solvent. When the collagen fiber aggregate or mass is included in the scaffold material, the portion serves as a dead end to suppress the infiltration of cells, blood vessels, and the like. The collagen fiber suspension is desirably prepared in water in a neutral region but, for example, the collagen fiber suspension may be obtained by preparing a solution of collagen molecules in an acidic region having a pH of 3 to less than 6.5 and adjusting the pH of the solution to a neutral region to convert the collagen molecules into collagen fibers.

The concentration of the collagen fibers is, for example, in terms of % by weight, about 0.3 to 8%, preferably about 0.5 to 6%, more preferably about 1 to 5%, still more preferably about 1 to 4%, particularly preferably about 1 to 3%. When the concentration of the collagen fibers is too high, there is a tendency for the viscosity to become high and the degree of orientation to become low. When the concentration of the collagen fibers becomes high, the diameter of each of the collagen fibers in the scaffold material becomes large and the strength becomes high, but the pore diameter is not largely affected.

Figure 3:
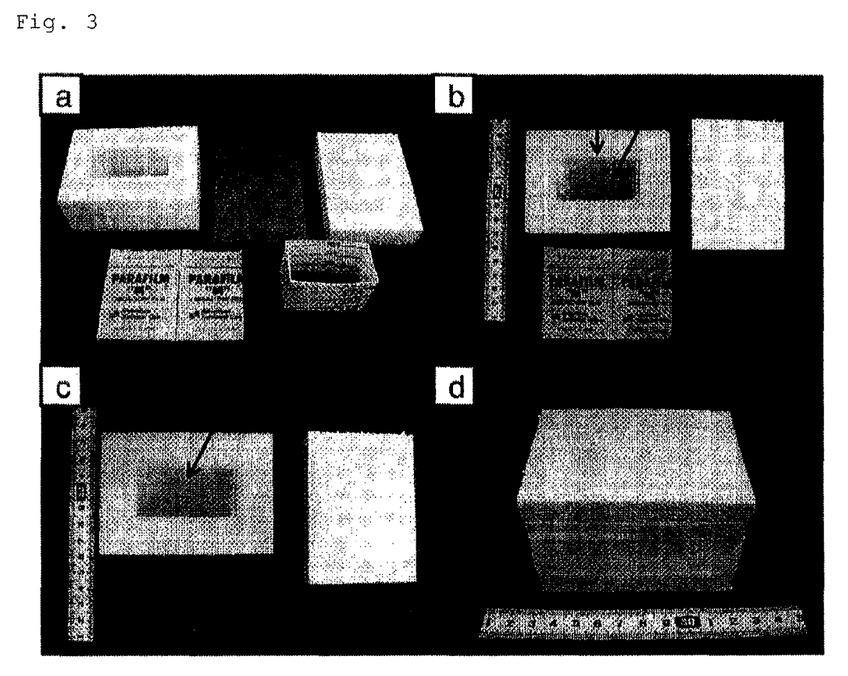

The collagen fiber suspension is preferably placed in a container that can be cooled from one surface, frozen, and then freeze-dried. For example, FIG. 3 show a container that has a bottom surface constructed of an aluminum plate and can be cooled only from the bottom surface. When the collagen fiber suspension is placed in such a container and frozen, the collagen fibers can be oriented in a vertical direction from the bottom surface. The freezing temperature varies depending on the size of the container, the concentration of the collagen fibers, and the like. The freezing temperature is not particularly limited but is, for example, about −80° C. to −1° C., preferably about −50° C. to −3° C., more preferably about −30° C. to −5° C., particularly preferably about −20° C. to −5° C. When the freezing temperature is too low, the pore diameter of the porous scaffold material becomes small, and the infiltration of cells, blood vessels, and the like into the scaffold material becomes slow or inhibited. For example, when the collagen fiber suspension was instantly frozen at −196° C., the pore diameter became too small, with the result that cells, blood vessels, and the like hardly infiltrated the scaffold material. In the case of the collagen fiber suspension having a concentration of about 3% in the small container shown in FIG. 3, the freezing temperature was found to be preferably about −20° C. to −10° C., particularly preferably about −10° C.

After having been frozen, the collagen fiber suspension is freeze-dried and then subjected to thermal processing. The freeze drying may be carried out in accordance with an ordinary method. The resultant freeze-dried product may be subjected to thermal processing at about 100° C. to 180° C., preferably about 120° C. to 150° C. for about 0.5 to 48 hours, preferably about one to 24 hours, more preferably about two to 12 hours, to thereby perform the thermal cross-linking of the collagen fibers. Cross-linking conditions may be appropriately selected so that the scaffold material at least partially maintains its shape during the acute phase of about two weeks when embedded into a living body, almost no foreign-body giant cells or no foreign-body giant cells were identified in the scaffold material, and almost no foreign-body reaction occurs. For example, the preferred conditions are thermal processing at 140° C. for six hours.

Even when the scaffold material has a sufficiently large pore diameter such as 100 to 300 µm, the presence of the foreign-body reaction causes the infiltration of cells and blood vessels into the scaffold material to proceed slowly or to hardly occur. Therefore, it is very important to eliminate the foreign-body reaction. Meanwhile, the scaffold material of the present invention is used by being embedded into an organ or tissue defect site or the like and infiltrated with the surrounding cells, blood vessels, and the like to regenerate the defect site. The scaffold material must be capable of wholly or at least partially maintaining its shape during the period for the infiltration and fixation of the surrounding cells, blood vessels, and the like, into the scaffold material (acute phase), for example, about two weeks. It has become evident that the implant material of the present invention achieves these two conflicting demands at high levels and thus allows tissue/organ regeneration to be satisfactorily performed. Depending on a site to be regenerated, various cells (e.g., stem cells or precursor cells, such as iPS cells, mesenchymal stem cells, saliva gland stem cells, hematopoietic stem cells, neural stem cells, liver precursor cells, pancreatic islet precursor cells, skin tissue stem cells, adipocyte precursor cells, or umbilical cord blood cells, or cells useful for organ or tissue repair/regeneration) may be used by being incorporated into the scaffold material of the present invention, proliferated, and then embedded into a site requiring tissue or organ repair or regeneration.

EXAMPLES

The present invention will be described in detail by using Examples.

Example 1

A Method for Producing a Denatured Collagen Fiber Scaffold Material

A collagen mass having a pH of 7 was produced from NMP collagen PS (Nippon Meat Packers) in accordance with a protocol (70% to 80% of type 1 and 30% to 20% of type III). The mass was crushed with a grater to a size of about 2×2×2 mm³, and 6 g of the crushed mass was added to 200 mL of sterilized Milli-Q water. After the addition, the mixture was stirred in a Hybrid Mixer (Keyence HM-500) for two minutes, and then sufficiently cooled in a refrigerator at 4° C. for 30 minutes or more. This process was repeated five times to produce a 3% w/v uniform collagen fiber suspension. Further, the suspension was left to stand still in a refrigerator at 4° C. for 12 hours to create a uniform suspension. After that, the pH was adjusted to 7.4 and then the collagen fiber suspension was further stirred in an Ace Homogenizer (Nissei HM-500) at 5,000 rpm for 30 minutes. This allowed the internal structure of the resultant collagen fiber scaffold material to become uniform. The suspension, which became paste-like, was poured into a container (FIG. 3) and cooled in a freezer at −10° C. for 12 hours. After the freezing, the frozen suspension was dried in a freeze drier for three days and then subjected to thermal denaturation processing (under the conditions shown in Table 1 below) under low pressure ($1\times10^{-1}$ Pa) to produce a denatured collagen fiber scaffold material.

Conditions for Producing Denatured Collagen Fiber Scaffold Material

TABLE 1

| pH | Denaturation temperature (° C.) | Processing time (H) |
|---|---|---|
| 7.4 | 50 | 6 |
| 7.4 | 100 | 6 |
| 7.4 | 100 | 24 |
| 7.4 | 110 | 6 |
| 7.4 | 120 | 6 |
| 7.4 | 120 | 24 |
| 7.4 | 130 | 6 |
| 7.4 | 140 | 0 (=No crosslink) |
| 7.4 | 140 | 6 |
| 7.4 | 140 | 9 |
| 7.4 | 140 | 12 |
| 7.4 | 140 | 24 |
| 7.4 | 170 | 5 |
| 7.4 | 170 | 6 |

Evaluation Method

Figure 4:
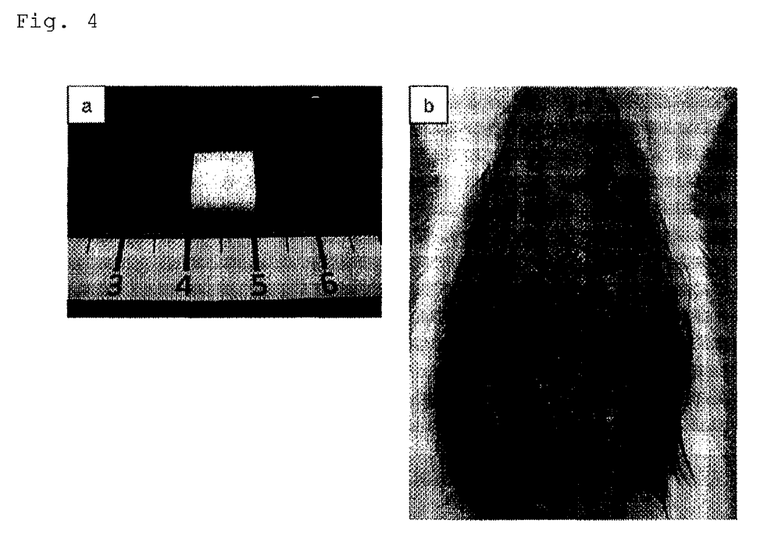
FIG. 4 shows a collagen fiber scaffold material and the appearance immediately after the collagen fiber scaffold material under the skin.
a: A collagen fiber scaffold material formed and processed into 1 cm×1 cm×5 mm.
b: The appearance immediately after the collagen fiber scaffold material was embedded under the back skin of a rat.

Collagen fiber scaffold materials were produced by using the above method and cut out into a size of 1 cm×1 cm×5 mm. Each collagen fiber scaffold material was embedded under the back skin of three rats (FIG. 4) and evaluated for the following two items after two weeks.

(I) Evaluation Method for Strength

A scaffold material must remain in the body to some extent for tissue regeneration. Accordingly, to what extent the embedded scaffold remained was evaluated by using a score. Table 2 shows the results.

Strength Score
1: The thickness is 0 mm. In other words, no collagen fiber scaffold material remains.
2: The collagen fiber scaffold material remains, but the thickness is 1 mm or less.
3: The thickness is 1 mm or more.

In general, a tissue shrinks during the production process for a specimen on a prepared slide. In other words, even when a tissue specimen containing a collagen fiber scaffold material having a thickness of 5 mm immediately after the embedding under the skin is produced, the thickness of the specimen on the prepared slide becomes less than 5 mm. Therefore, the thickness of the collagen fiber scaffold material two weeks after the embedding under the skin is actually larger than that on the prepared slide. In this experiment, the evaluation by using a score was performed based on the thickness of the specimen on the prepared slide.

(II) Evaluation Method for Biocompatibility

Figure 5:
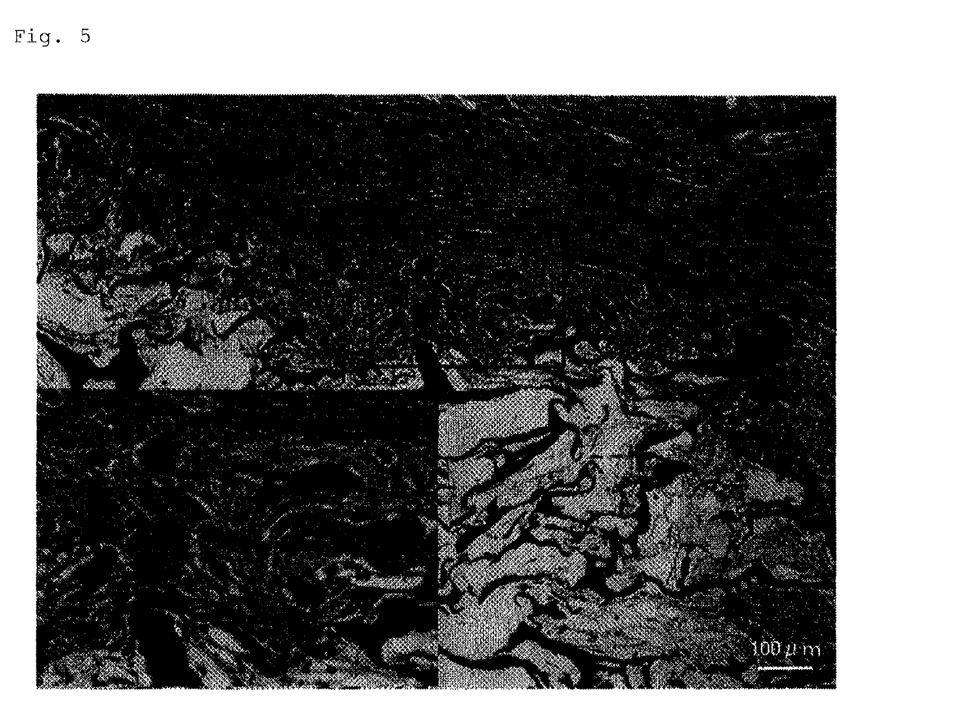
FIG. 5 shows foreign-body giant cells identified when a collagen fiber scaffold material having poor tissue compatibility is embedded under the skin. Foreign body giant cells with multiple nuclei are identified in the part enclosed with a square. The lower-left figure is an enlarged view of that part (HE staining).

When the living body recognizes an object invading the body as a foreign body, macrophages are dispatched to eliminate the object. In the case of a larger foreign body, the macrophages fuse and become a foreign-body giant cell to eliminate the foreign body. In other words, the presence of foreign-body giant cells indicates that the object surrounded by the cells has been recognized as a foreign body by the living body (FIG. 5). Therefore, the "degree of foreign body" of the scaffold material was evaluated by using the following score. Table 2 shows the results.

Compatibility Score
1: Foreign body giant cells are identified in the entire portion around the embedded collagen fiber scaffold material.
2: Foreign body giant cells are identified in only a portion around the embedded collagen fiber scaffold material.
3: Almost no foreign-body giant cells are identified around the embedded collagen fiber scaffold material.

TABLE 2

| pH | Denaturation temperature (° C.) | Processing time (H) | Strength score | Compatibility score |
|---|---|---|---|---|
| 7.4 | 50 | 6 | 1 | Impossible to evaluate (3) |
| 7.4 | 100 | 6 | 1 | Impossible to evaluate (3) |
| 7.4 | 100 | 24 | 1 | Impossible to evaluate (3) |
| 7.4 | 110 | 6 | 1 | Impossible to evaluate (3) |
| 7.4 | 120 | 6 | 1 | Impossible to evaluate (3) |
| 7.4 | 120 | 24 | 2 | 1 |
| 7.4 | 130 | 6 | 1 | Impossible to evaluate (3) |
| 7.4 | 140 | 0 (=No crosslink) | 1 | Impossible to evaluate (3) |
| 7.4 | 140 | 6 | 2 | 3 |
| 7.4 | 140 | 9 | 3 | 2 |
| 7.4 | 140 | 12 | 3 | 1 |
| 7.4 | 140 | 24 | 3 | 1 |
| 7.4 | 170 | 5 | 3 | 1 |
| 7.4 | 170 | 6 | 3 | 1 |

Figure 6:
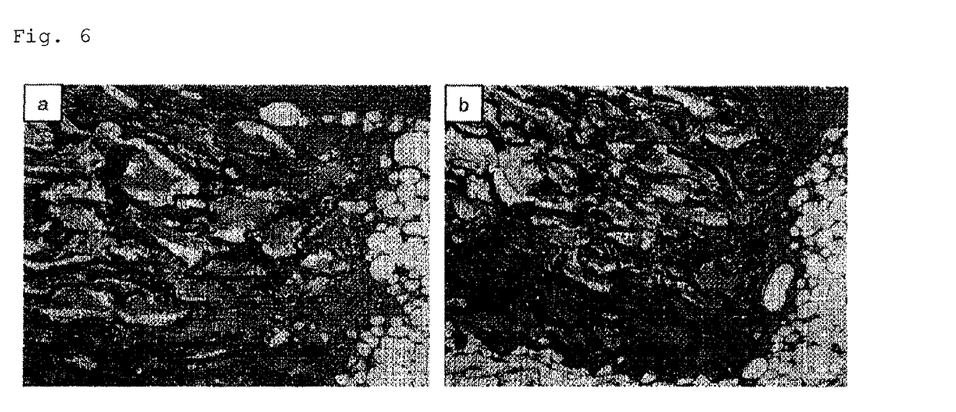

Table 2 reveals that the production conditions for a collagen fiber scaffold material that maintains a strength with a strength score of 2 or more and exhibits a compatibility score of 3 in vivo even two weeks after the embedding under the skin are the conditions of a denaturation temperature of 140° C. and a processing time of six hours. The second highest tissue compatibility was exhibited under the conditions of a denaturation temperature of 140° C. and a processing time of nine hours (FIG. 6). No tissue compatibility was exhibited under the conditions of a denaturation temperature of 140° C. and a processing time of 12 hours or more.

The comment "impossible to evaluate" in Table 2 means that it is impossible to evaluate the collagen fiber scaffold material because it has already dissolved at the time point of two weeks after the embedding under the skin. However, this means insufficient denaturation, leading to satisfactory tissue compatibility. Thus, the comment "impossible to evaluate" was considered to indicate a compatibility score of 3.

Discussion

Figure 7:
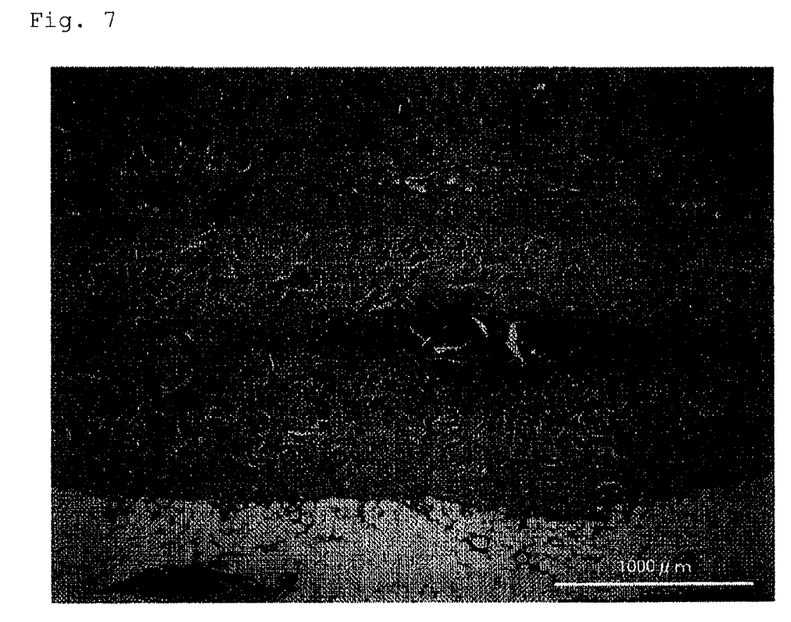
FIG. 7 shows a collagen fiber scaffold material not subjected to thermal denaturation processing (one week after the embedding under the skin). No foreign-body giant cells are identified around the scaffold material. Since pores in the scaffold material are not maintained, the infiltration property of cells is poor (HE staining).
Figure 8:
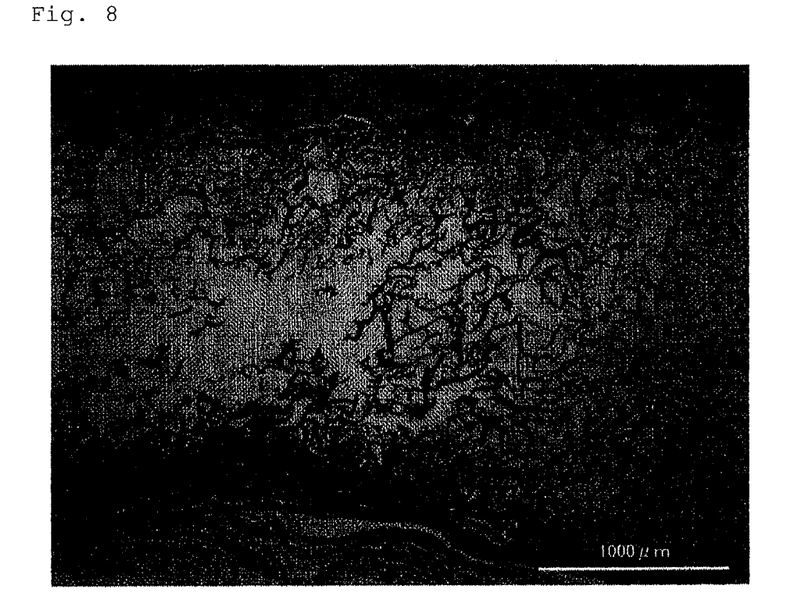
FIG. 8 shows a collagen fiber scaffold material subjected to thermal denaturation processing at 140° C. for 24 hours (two weeks after the embedding under the skin). Foreign body giant cells are identified around the scaffold material, and the infiltration property of cells is also poor (HE staining).

A collagen molecule is called "tropocollagen" and is constructed of an assembly of three polypeptide chains (α-chains) formed of about 1,000 amino acid residues. Each of the three α-chains has a left-handed helical structure, but the assembly of the three α-chains has a gentle right-handed structure having a cycle of 104 Å as a whole. This structure is called a "coiled-coil structure" or a "superhelix structure". Five collagen molecules assemble to form a collagen microfibril, and these microfibrils assemble to form a collagen fibril. Collagen fiber is an assembly of these collagen fibrils. The main epitope of the collagen fiber is present in the portions of the nonspiral structural telopeptides present at both ends of the collagen molecule, and the remainder of the molecule differs little between animal classes. The collagen used in this experiment is atelocollagen, which is produced by eliminating the portions of the antigenic telopeptides with pepsin. When a collagen fiber scaffold material without thermal denaturation processing is embedded under the skin, the compatibility score at one week after embedding was 3, and it is understood that the tissue compatibility of atelocollagen is very high (FIG. 7). However, the collagen fiber scaffold material had low strength, was almost dissolved two weeks after the embedding under the skin, and could not maintain a sufficient space for tissue regeneration. On the other hand, when a collagen fiber scaffold material was subjected to denaturation processing at 140° C. for 24 hours, the strength was increased and a sufficient space for tissue regeneration was maintained, but the antigenicity of the collagen fiber scaffold material was increased. In other words, the collagen fiber scaffold material was recognized as a foreign body for the living body with lowered tissue compatibility (FIG. 8). Thus, it was found that the strength is inversely proportional to the tissue compatibility. That is, the conditions found in this experiment can be said to suppress the antigenicity that is caused by the denaturation of the collagen fiber scaffold material as much as possible, and to provide some degree of strength. Thus, the processing time is estimated to be about six hours at levels equal to or higher than line A and equal to or higher than line B in the figure (FIG. 9).

Figure 10:
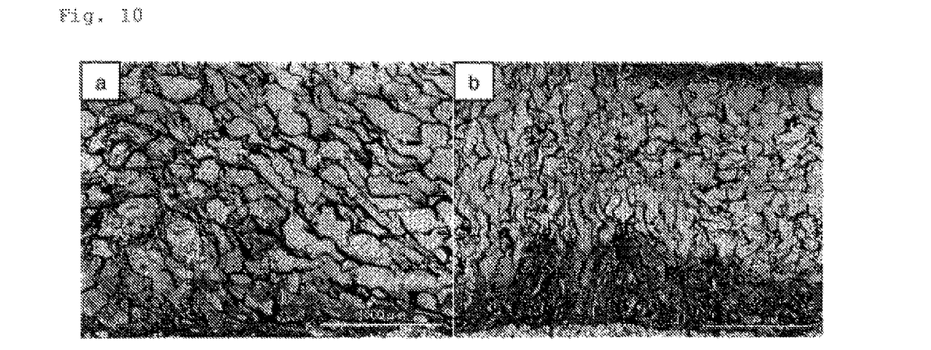
FIG. 10 shows collagen fiber scaffold materials subjected to thermal denaturation processing at 140° C. for 24 hours (one week after the embedding under the skin). Under these thermal denaturation processing conditions, the tissue compatibility of the collagen fiber scaffold material is poor. Even then, when collagen fiber orientation is provided to the scaffold material, cells infiltrate the scaffold material along collagen fibers to some extent (HE staining).
a: A scaffold material without collagen fiber orientation.
b: A scaffold material with collagen fiber orientation.

When cells infiltrate the collagen fiber scaffold material, the cells infiltrate along collagen fibers (FIG. 10). Therefore, when orientation is provided to the collagen fibers in the scaffold material, the infiltration property of cells into the scaffold material is improved. This improvement is also likely to lead to the ease of neovascularity. It is important to ensure blood flow around the region of tissue regeneration to maintain the infiltrated cells. In addition, when a collagen fiber scaffold material containing disseminated cells is implanted in the region of tissue regeneration, neovascularity in the early phase of the implantation in the scaffold material is required to maintain the viability of the disseminated cells. Therefore, the orientation of the collagen fibers in the scaffold material is considered to advantageously act on tissue regeneration.

Figure 11:
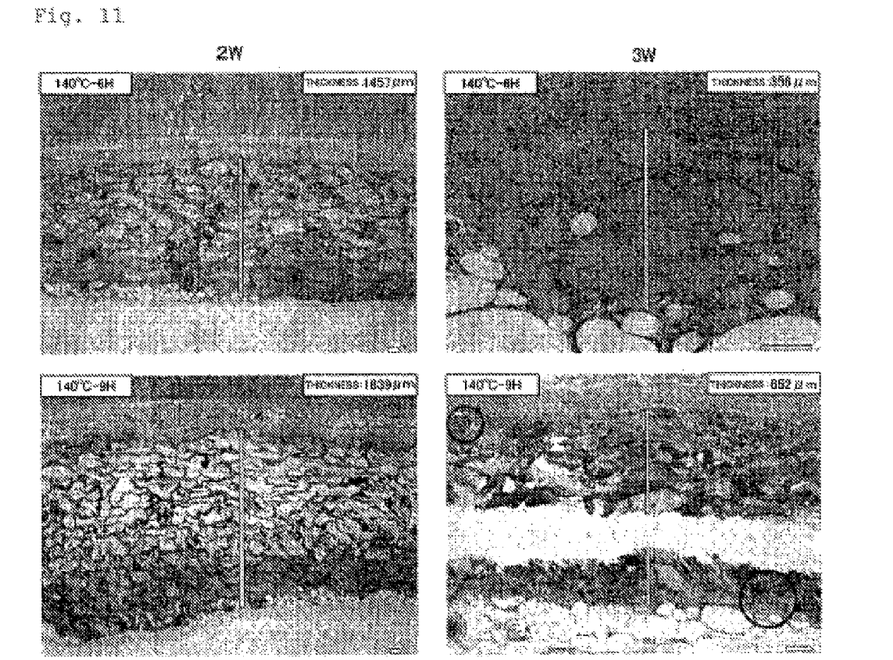
FIG. 11 shows comparisons between collagen fiber scaffold materials subjected to thermal denaturation processing two weeks and three weeks after the embedding under the skin. The two figures on the left show tissue findings two weeks after the embedding under the skin. The two figures on the right show tissue findings three weeks after the embedding under the skin. In each of the figures, thermal denaturation processing conditions are indicated on the upper-left part, and the thickness of the scaffold material is indicated on the upper-right part. The parts circled with yellow indicate sites at which foreign-body giant cells are identified (HE staining). In the lower-right photograph, a crack has occurred at the central portion of the scaffold in the production of a section, and thus the thickness is the sum of the upper and lower thicknesses.

In this example, it was concluded that the production conditions for a collagen fiber scaffold material to have a strength required for a scaffold for tissue regeneration and to have excellent tissue compatibility were the conditions of a denaturation temperature of 140° C. and a processing time of six hours. Further, it was inferred that the second desired production conditions were a denaturation temperature of 140° C. and a processing time of nine hours. When scaffold materials produced under the two sets of conditions were evaluated two weeks and three weeks after the embedding under the skin, the scaffold material processed at 140° C. for nine hours had a larger thickness both after two weeks and after three weeks, whereas the scaffold material processed at 140° C. for six hours had improved tissue compatibility compared to the scaffold material processed at 140° C. for nine hours and the improvement was larger after three weeks than after two weeks. In the scaffold material processed at 140° C. for nine hours, foreign-body giant cells were identified even three weeks after the embedding under the skin (FIG. 11). This demonstrated again that the tendency in FIG. 9 was true, and revealed that the scaffold material processed at 140° C. for six hours maintained tissue compatibility.

Figure 9:
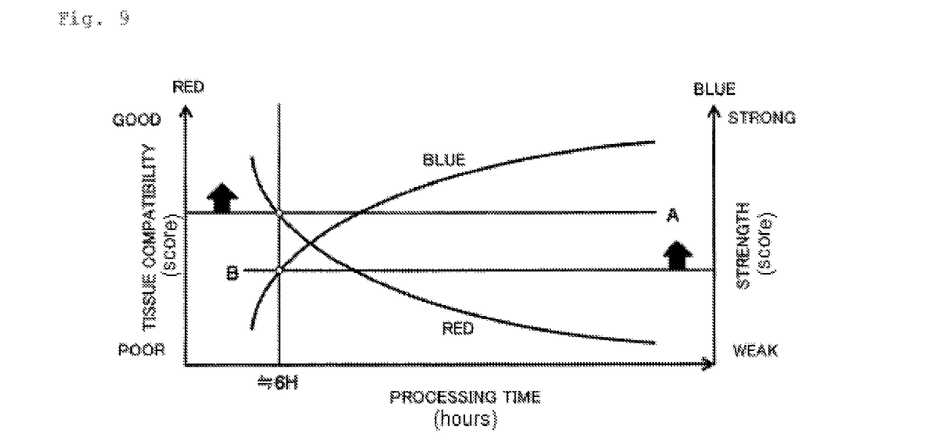
FIG. 9 shows the tendency of relationships between thermal denaturation processing times and the strength and tissue compatibility of a collagen fiber scaffold material (when the denaturation temperature is 140° C.). The red line represents the tissue compatibility, and the blue line represents the strength. Line A represents the lowest level of the tissue compatibility required for the scaffold material, and line B represents the lowest level of the strength required for the scaffold material. A short processing time results in poor strength but good tissue compatibility. In contrast, a long processing time results in increased strength but poor tissue compatibility because the scaffold material is recognized as a foreign body.
Figure 12:
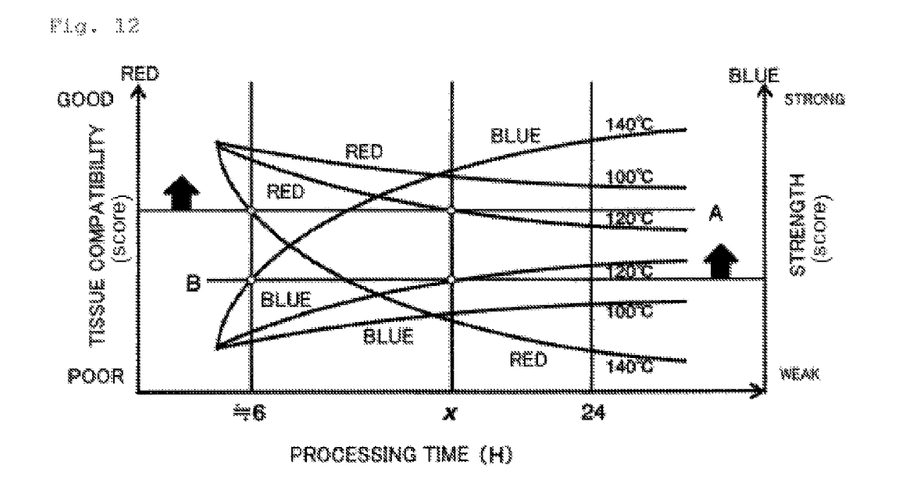
FIG. 12 shows the tendency of relationships between thermal denaturation processing times and the strength and tissue compatibility of a collagen fiber scaffold material (when the denaturation temperature is 100° C., 120° C., and 140° C.). The red and blue lines and lines A and B represent the same as in FIG. 9. The time x represents a processing time when a denaturation temperature is 120° C., which is estimated to allow the production of a scaffold material similar to that on processing conditions of 140° C. for six hours.

The lines of denaturation temperatures 100° C. and 120° C. are added to FIG. 9 based on the results (FIG. 12). From the figure, it is inferred that even when the denaturation temperature is 120° C., a processing time x providing a scaffold material with durability and maintained tissue compatibility is present between six hours or more and less than 24 hours. That is, there seem to be some other production conditions for a scaffold material similar to the scaffold materials produced in this experiment. The conditions of 140° C. for six hours are given as an example of the conditions. According to other experimental results in which a scaffold material processed at a denaturation temperature of 50° C. for a processing time of 48 hours was examined, the tissue compatibility was maintained but the strength was low. However, also in this case, when the processing time is set to 48 hours or more, there is possibility that a scaffold material similar to the scaffold materials obtained in this experiment will be obtained.

Example 2

Figure 13:
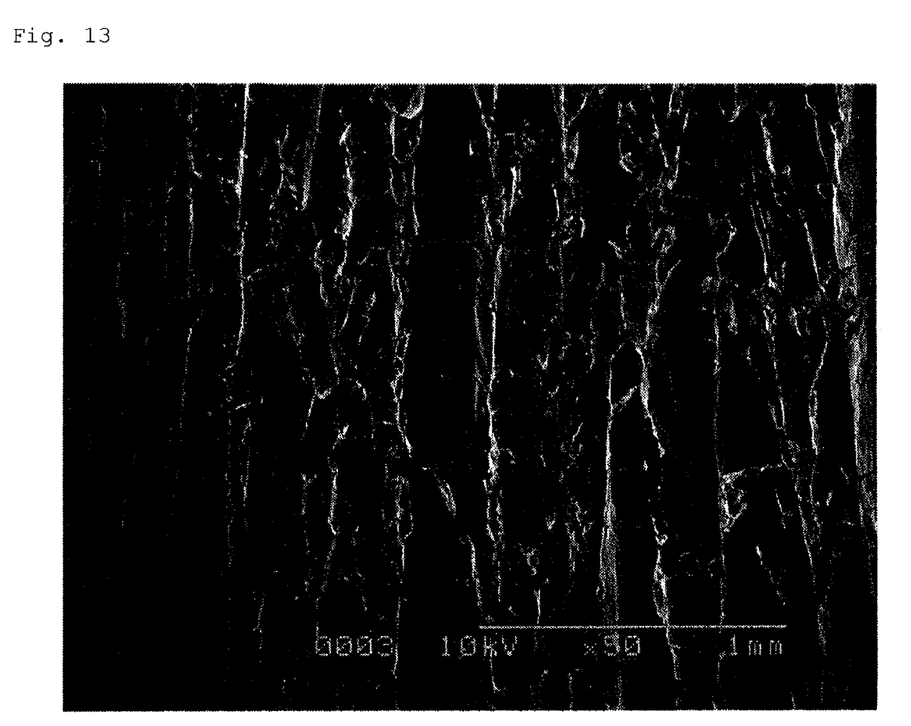
FIG. 13 is a vertical sectional view of a porous scaffold material of the present invention obtained in Example 2.

FIG. 13 shows a SEM photograph of the vertical section of a scaffold material obtained from a collagen fiber suspension containing collagen fibers at a concentration of 3% by weight under the conditions of a freezing temperature of −20° C. and thermal processing at 140° C. for six hours.

As shown in FIG. 13, it is clear that the porous scaffold material of the present invention has a structure in which the collagen fibers are oriented in one direction and pores are formed along the collagen fibers.

Example 3

A plurality of porous scaffold material samples obtained by carrying out denaturation processing at 140° C. for six hours in accordance with the production conditions described in Example 1 were each cut out into a size of 10 mm×10 mm and a height of 5 mm and compressed with a compression tester (Compact Table-Top Tester EZ Test, EZ-S, 20N, Shimadzu Corporation) at a speed of 1 mm/min until the load reached 19 N to obtain a stress-strain curve. The compression modulus of elasticity was calculated as a ratio between a stress and a strain in a straight line at portion corresponding to a strain of near 0.5 in an elastic region on the curve. As a result, the compression modulus of elasticity was 0.29 MPa at minimum and 0.42 MPa at maximum, and the compression moduli of elasticity of all the samples fell within the range of 0.29 to 0.42 MPa. It was confirmed that all the samples had satisfactory strength and biocompatibility.

The invention claimed is:

1. A porous scaffold material consisting of collagen fibers orientated in one direction and a plurality of pores in each individual collagen fiber that are along the orientation direction of the collagen fibers, wherein said porous scaffold material is produced by a process comprising placing a collagen fiber suspension in a container, and cooling the collagen fiber suspension only from the bottom surface, followed by freeze drying at −20° C. to −5° C. and thermal denaturation at 140° C. for 6 to 9 hours to form cross-links within the produced porous scaffold material; the produced porous scaffold material causes substantially no foreign-body reaction for at least two weeks when embedded into a living body, and the produced porous scaffold material functions as a scaffold material and retains tissue compatibility for at least two weeks in vivo.

2. The porous scaffold material according to claim 1, wherein the porous scaffold material has a compression modulus of elasticity of from 0.05 to 1.0 MPa.

3. The porous scaffold material according to claim 2, wherein the porous scaffold material has a compression modulus of elasticity of from 0.17 to 0.6 MPa.

4. The porous scaffold material according to claim 1, wherein the porous scaffold material has a pore diameter of from 50 to 500 μm.

5. The porous scaffold material according to claim 1, wherein the collagen fibers comprise atelocollagen fibers.

6. The porous scaffold material according to claim 1, wherein the porous scaffold material contains no foreign-body giant cells.

* * * * *